United States Patent
Demuth et al.

(10) Patent No.: US 6,794,549 B2
(45) Date of Patent: Sep. 21, 2004

(54) CONTINUOUS ADIABATIC PROCESS FOR NITRATING CHLOROBENZENE

(75) Inventors: Ralf Demuth, Hilden (DE); Matthias Gotta, Köln (DE); Thomas Linn, Grevenbroich (DE); Hans-Martin Weber, Leverkusen (DE); Eberhard Zirngiebl, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/360,192

(22) Filed: Feb. 6, 2003

(65) Prior Publication Data

US 2003/0181771 A1 Sep. 25, 2003

(30) Foreign Application Priority Data

Feb. 13, 2002 (DE) .......................... 102 05 855

(51) Int. Cl.[7] ............................................. C07C 205/00
(52) U.S. Cl. ......................................... 568/937; 568/936
(58) Field of Search ................................. 568/936, 937

(56) References Cited

U.S. PATENT DOCUMENTS

| | | | |
|---|---|---|---|
| 3,957,890 A | 5/1976 | Schumacher | 260/646 |
| 3,979,467 A | 9/1976 | Schumacher | 260/646 |
| 4,453,027 A | 6/1984 | Vaidyanathan | 568/937 |
| 5,714,647 A | 2/1998 | Blank et al. | 568/937 |
| 6,242,657 B1 * | 6/2001 | Konig et al. | 568/936 |
| 6,586,645 B2 * | 7/2003 | Demuth et al. | 568/937 |

FOREIGN PATENT DOCUMENTS

| | | |
|---|---|---|
| EP | 0 779 270 | 12/1996 |
| EP | 1 234 814 | 11/2002 |
| WO | 99/23061 | 5/1999 |

OTHER PUBLICATIONS

Chemical Abstracts, vol. 133, No. 14, Oct. 2, 2000 Columbus, Ohio, US.
Abstract No. 192947y Lu, Chunxu et al.: "Regioselective nitration of chlorobenzene in nitri acid–sulfuric acid–phosphoric acid system." Speite 675; Spalte 2; XPOO2243420 Zusammenfassung & Huagong Shikan, Bd. 14, Nr. 3, 2000, Seiten 24–25.
Chemical Abstracts, vol. 116, No. 6, Feb. 10, 1992 Columbus, Ohio US.
Abstract No. 43403q, Wei, Wenlong et al.: "Technological improvement on nitration of chlorobenzene." Seite 103; Spalte 1; XPOO2243421 Zusammenfassung & Taiyuan Gongye Daxue Xuebao, Bd. 22, Nr. 2, 1991, Seiten 28–31.

* cited by examiner

*Primary Examiner*—J. Parsa
(74) *Attorney, Agent, or Firm*—Godfried R. Akorli; Diderico van Eyl

(57) ABSTRACT

The present invention relates to a continuous adiabatic process for preparing nitrochlorobenzene in the presence of phosphoric acid. The waste acid produced during the practice of the process is reconcentrated and recycled into the nitration reaction.

15 Claims, No Drawings

CONTINUOUS ADIABATIC PROCESS FOR NITRATING CHLOROBENZENE

BACKGROUND OF THE INVENTION

1. Field of the Invention

The present invention relates to a continuous adiabatic process for preparing nitrochlorobenzene, where the waste acid produced during the practice of the process is reconcentrated and recycled into the nitration reaction. By adding phosphoric acid, it is possible to increase significantly the proportion of the product of value ortho-nitrochlorobenzene. The production of the co-product para-nitrochlorobenzene is suppressed in favour of the product of value.

2. Brief Description of the Prior Art

Nitrochlorobenzenes are important intermediates in the preparation of dyes, pharmaceuticals and pesticides. There is a particularly high demand for ortho-nitrochlorobenzene, which is obtained, in the customary nitration of chlorobenzene in about 35%. para-Nitrochlorobenzene, too, has a number of industrial uses. Since there are only very limited industrial applications for meta-nitrochlorobenzene, its production is generally undesired.

Industrially, nitrochlorobenzenes are prepared by nitration of chlorobenzene. For nitration, it is customary to use a mixture of sulphuric acid, nitric acid and water. Under these conditions, the proportion of the para-isomer is very high. The ratio of para- to ortho-nitrochlorobenzene is usually about 1.95. Additionally, a considerable proportion of waste sulphuric acid contaminated with organic compounds is produced, requiring complicated and expensive work-up. The reconcentration of the waste sulphuric acid succeeds in a particularly elegant manner when the nitration reaction is carried out under adiabatic conditions, since in this case, there is no heat exchange with the environment, and the energy released during the process can be used to preheat and/or reconcentrate the waste sulphuric acid. Moreover, under adiabatic conditions, it is possible to obtain a considerably improved ratio of para- to ortho-nitrochlorobenzene. If part of the sulphuric acid is replaced by phosphoric acid, it is possible to obtain a considerably improved ratio of para- to ortho-nitrochlorobenzene whilst maintaining the energetically favourable conditions for reconcentrating the waste acid.

The effect of phosphorous compounds on nitrations is described in the literature. Thus, DE 2 422 305 describes the addition of phosphoric acid in the isothermal nitration of chlorobenzene and the associated higher yield of ortho-nitrochlorobenzene. Here, in general, the use of phosphoric acid is accompanied by a reduced rate of reaction. To obtain economical space-time yields, it is necessary to employ highly concentrated phosphoric acids (>100% $H_3PO_4$). However, the reconcentration and recycling of these phosphoric acids is very complicated. Alternatively, the nitration may also be carried out at an elevated reaction temperature. However, this results inter alia in a higher proportion of unwanted m-nitrochlorobenzene which has to be removed at high cost.

U.S. Pat. No. 4,453,027 claims an adiabatic nitration process for the preparation of mononitrohalobenzenes. However, the nitrating acid used contains such large amounts of nitric acid that, although the end temperature described is from 100 to 110° C., the start temperature of the reaction, and consequently of the reactants, has to be from 0 to 10° C. Such a process is neither technically nor economically sensible, since cooling brine and expensive apparatus have to be used.

EP 675 104 A describes an adiabatic process for the nitration of halobenzenes, where the reactants are mixed with application of a certain mixing energy and mixing is carried out in a temperature range of from 60 to 160° C. Using the temperatures mentioned, it is possible to obtain the high reaction rates required for adiabatic operation. However, this process has the disadvantage that relatively high proportions of unwanted meta-nitrochlorobenzene are obtained, the removal of which, as already mentioned, is complicated and costly.

Accordingly, there was a need for a process for the continuous preparation of nitrochlorobenzene, which process permits easy work-up and recycling of the waste acid and a considerably improved yield of the target product ortho-nitrochlorobenzene, substantially avoiding the unwanted byproduct meta-nitrochlorobenzene.

SUMMARY OF THE INVENTION

Surprisingly, we have now found a process for the continuous preparation of nitrochlorobenzene by reacting chlorobenzene with sulphuric acid, phosphoric acid, nitric acid and water, which process is characterized in that a) the feedstocks chlorobenzene, sulphuric acid, phosphoric acid and water are introduced simultaneously or successively in any order into a reactor equipped with mixing elements and are mixed such that the temperature of the reaction mixture during initial mixing is from 10 to 80° C., b) the content of phosphoric acid in the reaction mixture during mixing, based on the sum of sulphuric acid, phosphoric acid, nitric acid and water, is from 10 to 50% by weight, c) the reaction proceeds under adiabatic conditions, d) at the reactor outlet, the crude nitrochlorobenzene is separated from the waste acid and e) the waste acid is reconcentrated and recycled as a recycled acid mixture into the nitration reaction and f) if appropriate, up to 3000 ppm of a silicon compound may be added.

DETAILED DESCRIPTION OF THE INVENTION

The feedstocks used in the process according to the invention are chlorobenzene, sulphuric acid, phosphoric acid, nitric acid and water, where the chlorobenzene used may contain nitrochlorobenzene in an amount of, for example, from 0 to 20% by weight. A higher amount is possible, but uneconomical. Here, water can be used as such or else is introduced into the reaction as dilution water in the nitric acid and/or the sulphuric acid and/or the phosphoric acid.

In the process according to the invention, feedstock chlorobenzene, sulphuric acid, phosphoric acid, nitric acid and water can be introduced individually or as mixtures into a reactor equipped with mixing elements. The feedstocks can be introduced into the reactor simultaneously or successively in any order. Introduction in to the reactor can be carried out, for example, by adding chlorobenzene and nitric acid, and, if appropriate, water as separate streams simultaneously or successively to the recycled acid mixture, where the nitric acid may be diluted with water. It is also possible to pre-mix chlorobenzene with water and sulphuric acid and/or phosphoric acid and to introduce the resulting mixture as a separate stream into the reactor. Mixing of nitric acid, with sulphuric acid and/or phosphoric acid and/or water, takes place in the reactor. It is furthermore possible to introduce chlorobenzene and a nitrating acid prepared by mixing sulphuric acid, phosphoric acid, nitric acid and, if appropriate, water in separate streams into the reactor. In a preferred embodiment of the process according to the invention, nitric acid and the recycled acid mixture are mixed to give a nitrating acid, and nitrating acid and chlorobenzene are introduced into the reactor in separate streams. For the reaction to succeed, the reactants are introduced into the reactor, such that the reaction mixture obtained once all reactants have been mixed has the composition according to the invention and mixing takes place at the temperature according to the invention.

At the time of mixing, the content of phosphoric acid, based on pure $H_3PO_4$ in the reaction mixture, based on the sum of sulphuric acid based on pure $H_2SO_4$, phosphoric acid based on pure $H_3PO_4$, nitric acid based on pure $HNO_3$ and water, may be from 10 to 50% by weight, preferably from 15 to 50% by weight and particularly preferably from 20 to 45% by weight.

At the time of mixing, the content of sulphuric acid, based on pure $H_2SO_4$ in the reaction mixture, based on the sum of sulphuric acid based on pure $H_2SO_4$, phosphoric acid based on pure $H_3PO_4$, nitric acid based on pure $HNO_3$ and water, may be from 30 to 80% by weight, preferably from 40 to 75% by weight and particularly preferably from 40 to 65% by weight. Sulphuric acid can be employed, for example, with a content of from 65 to 100% by weight of sulphuric acid, preferably from 80 to 100% by weight.

At the time of mixing, the content of nitric acid, based on pure $HNO_3$, based on the sum of sulphuric acid based on pure $H_2SO_4$, phosphoric acid based on pure $H_3PO_4$, nitric acid based on pure $HNO_3$ and water, may be from 3 to 10% by weight, preferably from 4 to 8% by weight and particularly preferably from 4 to 6% by weight. Nitric acid can be employed, for example, with a content of from 60 to 98% by weight of nitric acid, but is preferably used in the form of concentrated nitric acid of from about 60 to 70% by weight.

At the time of mixing, the content of water in the reaction mixture, based on the sum of sulphuric acid based on pure $H_2SO_4$, phosphoric acid based on pure $H_3PO_4$, nitric acid based on pure $HNO_3$ and water, may be from 5 to 30% by weight, preferably from 5 to 20% by weight and particularly preferably from 8 to 18% by weight.

Per mole of chlorobenzene, from 0.5 to 2 moles, preferably from 1.0 to 1.3 mol, particularly preferably from 1.0 to 1.2 mol and very particularly preferably from 1.05 to 1.1 mol, of nitric acid, based on pure $HNO_3$ can be used. In a preferred embodiment of the process according to the invention, the reactants are mixed such that the average mixing power density in the reactor is from 1.5 to 40 watt/l, preferably from 1.5 to 30 watt/l. For mixing, it is possible to use the mixing elements known in the art, for example static mixers, pumps, nozzles, stirrers or combinations thereof. The mixing power density, expressed in watts per litre, in a continuously operated reactor is determined as follows:

Mixing power density=power $P$/volume $V$ [W/l]

$P$=throughput of the reactants $[m^3/s]$×dynamic pressure drop $\Delta P_{dyn} [N/m^2]$ $\Delta P_{dyn}$=total pressure drop $\Delta P_{total}$-static pressure drop $\Delta P_{stat}$ Since the average mixing power density acts on each litre of the reaction mixture and this reaction mixture is present only in the reactor, the volume of the reactor in which the reaction is carried out is used as volume V when calculating the average mixing power density.

If parts of the reactor or its components are made of enamel or the reaction mixture comes into contact with enamelled parts, it is advantageous to add silicon compounds. The amount may, for example, be up to 3000 ppm and is preferably between 10 and 3000 ppm and particularly preferably between 50 and 300 ppm, the amount being based on ppm by mass based on the weight of the reaction mixture. This additive suppresses the attack on enamel by phosphoric acid, at least substantially. Here, the various modifications of silicas and silicic acids, such as, for example, water glass, precipitated silica or Aerosil can be used.

During initial mixing, the temperature of the reaction mixture can, by way of example and by way of preference, be from 10 to 80° C., particularly preferably from 20 to 50° C. and very particularly preferably from 30 to 45° C. Depending on the temperature during initial mixing and on the conversion, the final temperature generally does not exceed 130° C. and is preferably between 80 and 100° C. The reaction should preferably proceed without any backmixing, which can be achieved, for example, by dispersing the reaction mixture. This is preferably carried out by internals or elements provided in the reactor for this purpose, such as, for example, perforated metal sheets, slotted metal sheets, impact baffles, vanes, baffleplates, static mixers or stirrers.

Continuously operated reactors suitable for the process according to the invention which may be mentioned are, for example: tubular reactors, preferably having internals for dispersing, such as, for example, perforated metal sheets, slotted metal sheets, impact baffles, vanes, baffle plates, static mixers, stirrers and the like, vigorously agitated kettles in cascade arrangement, loop reactors having the internals described above, combinations of a plurality of the apparatuses mentioned, further reactors acting in the same manner, such as chamber reactors having stirrers in each chamber. In the process according to the invention, preference is given to using tubular reactors having internals. Preferred internals are perforated metal sheets. All internals represent subdivisions of the entire apparatus which equally serve for dispersion and the substantial prevention of backmixing.

After the intensive mixing, after each dispersion or after the mixture has flowed through a certain path-length of the reactor, coalescence of the dispersion droplets, which is observed can be reversed by redispersion. The number of dispersion operations is preferably from 2 to 50, with preference from 3 to 30 and particularly preferably from 4 to 20. The average mixing power density of preferably 1.5 to 40 watt/l which, during mixing of the reactants, acts on each litre of the reaction mixture, is preferably used to overcome the pressure drops occurring during the dispersion operations.

According to the equation of the process according to the invention, chlorobenzene is reacted with nitric acid to give nitrochlorobenzene and water. Thus, chlorobenzene and nitric acid are introduced into the process, and nitrochlorobenzene and water are discharged; the sulphuric acid/phosphoric acid/water mixture described being the reaction medium. Since, in the case of industrial implementation, it is advantageous to use water-containing nitric acids, the water of the water-containing nitric acid used has to be discharged in addition to the water of the reaction.

In the process according to the invention, the crude nitrochlorobenzene is separated from the waste acid at the reactor outlet. The separation can be carried out in apparatus known to the person skilled in the art or with the aid of means which are sufficiently well known. Thus, separation may be effected, for example, using a static separator. The resulting waste acid is substantially free of nitric acid and contains mainly sulphuric acid, phosphoric acid and water, and possibly small amounts of organic impurities and/or nitrosylsulphuric acid. The concentrations of sulphuric acid, phosphoric acid and water in the waste acid are a function of the feedstock concentration and the stoichiometry of the reaction equation:

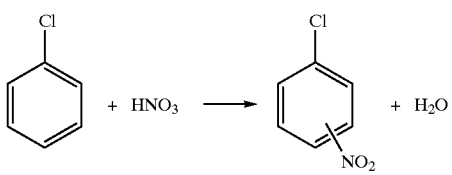

For re-use, the waste acid is, according to the invention, reconcentrated and advantageously recycled into the nitration reaction. During reconcentration, water is removed by distillation. To this end, use is preferably made of the heat of the reaction taken up by the waste acid.

The reconcentration is preferably carried out in an evaporator which is preferably operated at a pressure of from 60 to 200 mbar, particularly preferably from 60 to 180 mbar and very particularly preferably from 80 to 150 mbar. Here, the temperature of the waste acid in the evaporator outlet is preferably from 100 to 200° C., particularly preferably from 130 to 190° C. and very particularly preferably from 145 to 165° C. The temperature of the reconcentrated waste acid which is discharged is preferably used to heat the waste acid flowing into the evaporator in a countercurrent heat exchanger.

In a preferred embodiment of the process according to the invention, the reconcentration removes approximately the same amount of water as the amount which is introduced into the reaction medium by the water of the reaction and, if appropriate, water-containing nitric acid.

The reconcentration is preferably carried out in a one-step process, using, preferably, a commercial cascade evaporator with tantalum tube bundle which, from the point of entry, the acid concentration is increased with each cascade, so that an acid having a relatively low concentration is present in the first cascades. It is an advantage of the low concentration of the first cascade that, firstly, the boiling point is still low, resulting in a high driving temperature difference for the heat transfer and, secondly, that at higher water concentrations it is easier to remove any nitrosylsulphuric acid present in the waste acid from the reaction. Thus, by using a cascade evaporator in the process according to the invention, it is possible to avoid the blowing out of nitrosylsulphuric acid with sulphur dioxide, which is usually carried out, and thus an additional process step. To prevent the formation of deposits of organic compounds, in particular nitrochlorobenzene, on the condenser, the condenser is, in a preferred embodiment, continuously sprinkled with chlorobenzene. The organic phase that has been discharged and comprises chlorobenzene and nitrochlorobenzene can be used as feedstock for the process according to the invention.

The process according to the invention has the advantage that, by using a mixture of phosphoric acid and sulphuric acid as reaction medium, it is possible to achieve a higher yield of ortho-nitrochlorobenzene and to recycle the waste acid as a recycled acid mixture in a technically favourable manner.

EXAMPLES

Example 1

418 g of $H_2SO_4$ (100% strength), 167 g of phosphoric acid (85% strength), 61 g of water and 53.8 g of $HNO_3$ (65% strength) were, at 40° C., initially charged with stirring (specific stirring power input 22 W/l) into a heat-insulated sulphonation beaker (Ø100 mm), fitted with flow spoilers and two turbine mixers (Ø39.9 mm) mounted on a shaft, and over a period of 3 seconds, 68.7 g of chlorobenzene were added and reacted without cooling. After 120 seconds, the reaction mixture had reached the end temperature of 90° C. and the stirrer was stopped. Following phase separation, 85.3 g of organic phase were obtained.

| | |
|---|---|
| Chlorobenzene: | 5.32% by weight |
| ortho-Nitrochlorobenzene: | 37.19% by weight |
| meta-Nitrochlorobenzene: | 0.75% by weight |
| para-Nitrochlorobenzene: | 56.25% by weight |
| Dinitrochlorobenzenes: | 0.25% by weight |

The ratio para/ortho-nitrobenzene is 1.50.

The waste acid was, at 110 mbar and 150° C., reconcentrated to the original water content and again admixed with nitric acid. Following the procedure described above, another nitration was carried out, giving the same results. Even after the acid had been recycled several times, no loss of activity was observed.

Example 2

316.5 g of $H_2SO_4$ (100% strength), 323.0 g of phosphoric acid (85% strength), 6.5 g of water and 53.8 g of $HNO_3$ (65% strength) were, at 40° C., initially charged with stirring (specific stirring power input 22 W/l) into a heat-insulated sulphonation beaker (Ø100 mm), fitted with flow spoilers and two turbine mixers (Ø39.9 mm) mounted on a shaft, and over a period of 3 seconds, 68.7 g of chlorobenzene were added and reacted without cooling. After 160 seconds, the reaction mixture had reached the end temperature of 90° C. and the stirrer was stopped. Following phase separation, 83.9 g of organic phase were obtained.

| | |
|---|---|
| Chlorobenzene: | 5.59% by weight |
| ortho-Nitrochlorobenzene: | 38.30% by weight |
| meta-Nitrochlorobenzene: | 0.70% by weight |
| para-Nitrochlorobenzene: | 54.65% by weight |
| Dinitrochlorobenzenes: | 0.23% by weight |

The ratio para/ortho-nitrobenzene is 1.41.

The waste acid was, at 110 mbar and 150° C., reconcentrated to the original water content and again admixed with nitric acid. Following the procedure described above, another nitration was carried out, giving the same results. Even after the acid had been recycled several times, no loss of activity was observed.

Example 3

Not According to the Invention 646.2 g of $H_2SO_4$ (81% strength) and 53.8 g of $HNO_3$ (65% strength) were, at 40° C., initially charged with stirring (specific stirring power input 22 W/l) into a heat-insulated sulphonation beaker (Ø100 mm), fitted with flow spoilers and two turbine mixers (Ø 39.9 mm) mounted on a shaft, and over a period of 3 seconds, 68.7 g of chlorobenzene were added and reacted without cooling. After 135 seconds, the reaction mixture had reached the end temperature of 94° C. and the stirrer was stopped. Following phase separation, 87.8 g of organic phase were obtained.

| | |
|---|---|
| Chlorobenzene: | 6.25% by weight |
| ortho-Nitrochlorobenzene: | 34.43% by weight |
| meta-Nitrochlorobenzene: | 0.85% by weight |

| | |
|---|---|
| para-Nitrochlorobenzene: | 57.30% by weight |
| Dinitrochlorobenzene: | 0.14% by weight |

The ratio para/ortho-nitrobenzene is 1.62.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the continuous preparation of nitrochlorobenzene by a nitration reaction comprising reacting chlorobenzene with sulphuric acid, phosphoric acid, nitric acid and water, characterized in that
    a) feedstock chlorobenzene, sulphuric acid, phosphoric acid and water are introduced simultaneously or successively in any order into a reactor equipped with mixing elements and are mixed such that the temperature of the reaction mixture during initial mixing is from 10 to 80° C.,
    b) the content phosphoric acid, based on pure $H_3PO_4$, in the resulting reaction mixture during mixing, based on the sum of sulphuric acid, phosphoric acid, nitric acid and water, is from 10 to 50% by weight,
    c) the reaction proceeds under adiabatic conditions,
    d) at the reactor outlet, crude nitrochlorobenzene is separated from the waste acid,
    e) waste acid is reconcentrated in a one-step process and recycled into the nitration reaction.

2. Process for the continuous preparation of nitrochlorobenzene by a nitration reaction comprising reacting chlorobenzene with sulphuric acid, phosphoric acid, nitric acid and water, characterized in that
    f) feedstock chlorobenzene, sulphuric add, phosphoric acid and water are introduced simultaneously or successively in any order into a reactor equipped with mixing elements and are mixed such that the temperature of the reaction mixture during initial mixing is from 10 to 80° C.,
    g) the content phosphoric acid, based on pure $H_3PO_4$, in the resulting reaction mixture during mixing, based on the sum of sulphuric acid, phosphoric acid, nitric acid and water, is from 10 to 50% by weight,
    h) the reaction proceeds under adiabatic conditions,
    i) at the reactor outlet, crude nitrochlorobenzene is separated from the waste acid,
    waste acid is reconcentrated and recycled into the nitration reactiona, characterized in that it is carried out in the presence of silicon compounds.

3. Process according to claim 1, characterized in that the content of sulphuric acid, based on pure $H_2SO_4$, in the reaction mixture during mixing is from 30 to 80% by weight.

4. Process according to claim 1, characterized in that the content of nitric acid, based on pure $HNO_3$, in the reaction mixture during mixing is from 3 to 10% by weight, based on the sum or sulphuric acid, nitric acid and water.

5. Process according to claim 1, characterized in that the nitric acid is employed in the form of 60–70% strength nitric acid.

6. Process according to claim 1, characterized in that the content of water in the reaction mixture during mixing, based on the amount of sulphuric acid based on pure $H_2SO_4$, phosphoric acid based on pure $H_3PO_4$, nitric acid be on pure $HNO_3$ and water, is from 5 to 30% by weight.

7. Process according to claim 1, characterized in that the chlorobenzene is employed in an amount of from 1 to 1.3 mol per mole of nitric acid.

8. Process according to claim 1, characterized in that the chlorobenzene employed comprises nitrochlorobenzene in an amount of from 0 to 20% by weight.

9. Process according to claim 1, characterized in that the average mixing power density is from 1.5 to 40 watt/l.

10. Process according to claim 1, characterized in that the temperature of the reaction mixture during initial mixing is from 20 to 50° C.

11. Process according to claim 1, characterized in that the reconcentration of the waste acid is carried out in an evaporator.

12. Process according to claim 11, characterized in that the reconcentration of the waste acid in carried out in an evaporator at a pressure of from 60 to 200 mbar.

13. Process according to claim 11, characterized in that the temperature of the waste acid in the evaporator outlet is from 100 to 200° C.

14. Process according to claim 11, characterized in that the evaporator is a cascade evaporator with tantalum tube bundle.

15. Process according to claim 11, characterized in that the evaporator is a cascade evaporator.

* * * * *